United States Patent
Yaddanapudi et al.

(10) Patent No.: US 11,791,041 B2
(45) Date of Patent: *Oct. 17, 2023

(54) ACCEPTANCE, COMMISSIONING, AND ONGOING BENCHMARKING OF A LINEAR ACCELERATOR (LINAC) USING AN ELECTRONIC PORTAL IMAGING DEVICE (EPID)

(71) Applicants: Washington University, St. Louis, MO (US); The Regents of the University of California, Oakland, CA (US)

(72) Inventors: Sridhar Yaddanapudi, St. Louis, MO (US); Sreekrishna M. Goddu, St. Louis, MO (US); Sasa Mutic, St. Louis, MO (US); Todd Pawlicki, San Diego, CA (US)

(73) Assignees: Washington University, St. Louis, MO (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,230

(22) Filed: Jan. 23, 2023

(65) Prior Publication Data

US 2023/0154603 A1 May 18, 2023

Related U.S. Application Data

(60) Division of application No. 17/808,399, filed on Jun. 23, 2022, now Pat. No. 11,756,680, which is a (Continued)

(51) Int. Cl.
*G16H 40/40* (2018.01)
*A61N 5/10* (2006.01)

(52) U.S. Cl.
CPC .......... *G16H 40/40* (2018.01); *A61N 5/1075* (2013.01); *A61N 2005/1054* (2013.01)

(58) Field of Classification Search
CPC .......... A61N 2005/1054; A61N 5/1075; G06F 19/00; G06F 19/3412; G16H 40/40
See application file for complete search history.

(56) References Cited

U.S. PATENT DOCUMENTS

| 5,471,516 A | 11/1995 | Nunan |
| 6,626,569 B2 | 9/2003 | Reinstein et al. |

(Continued)

FOREIGN PATENT DOCUMENTS

| CN | 101610811 A | 12/2009 |
| CN | 102160470 A | 8/2011 |

(Continued)

OTHER PUBLICATIONS

Benjamin et al., "Evaluating IMRT and VMAT dose accuracy: Practical Examples of Failure to Detect Systematic Errors when Applying a Commonly Used Metric and Action Levels", 2013, Standard Imaging Publication, pp. 1-16 (Year: 2013).*

(Continued)

*Primary Examiner* — Elias Desta
(74) *Attorney, Agent, or Firm* — McKee, Voorhees & Sease, PLC

(57) ABSTRACT

The present invention is a method or system for acceptance testing and commissioning of a LINAC and treatment planning system (TPS). For a LINAC commissioning, the present invention collects reference data from a fully calibrated LINAC and compares the reference data with machine performance data collected from LINAC. The compared results are analyzed to assess accuracy of the testing LINAC. For a TPS commissioning, the present invention collects standard reference data from standard treatment plans and (Continued)

standard input data and compares the standard reference data with results from standard tests that are performed by a testing treatment plan system. The compares results are analyzed to assess accuracy of the testing treatment plan system.

13 Claims, 7 Drawing Sheets

Related U.S. Application Data continuation of application No. 17/212,065, filed on Mar. 25, 2021, now Pat. No. 11,393,582, which is a continuation of application No. 16/738,402, filed on Jan. 9, 2020, now Pat. No. 10,964,429, which is a division of application No. 15/320,599, filed as application No. PCT/US2015/036749 on Jun. 19, 2015, now Pat. No. 10,553,313.

(60) Provisional application No. 62/015,184, filed on Jun. 20, 2014.

(56) References Cited

U.S. PATENT DOCUMENTS

| | | | |
|---|---|---|---|
| 6,810,107 B2 | 10/2004 | Steinberg | |
| 6,810,108 B2 | 10/2004 | Clark et al. | |
| 7,801,269 B2 | 9/2010 | Cravens et al. | |
| 8,073,104 B2 | 12/2011 | Yan et al. | |
| 8,351,572 B1 | 1/2013 | Renner | |
| 10,553,313 B2 | 2/2020 | Yaddanapudi et al. | |
| 10,682,528 B2 | 6/2020 | Ansorge et al. | |
| 10,964,429 B2 * | 3/2021 | Yaddanapudi | G16H 40/40 |
| 11,393,582 B2 | 7/2022 | Yaddanapudi et al. | |
| 2002/0181660 A1 | 12/2002 | Reinstein et al. | |
| 2003/0086529 A1 | 5/2003 | Clark et al. | |
| 2003/0095625 A1 | 5/2003 | Steinberg | |
| 2008/0170671 A1 | 7/2008 | Wu | |
| 2011/0121763 A1 | 5/2011 | Sadler et al. | |
| 2012/0310615 A1 | 12/2012 | Moore et al. | |
| 2014/0019440 A1 | 1/2014 | Kim et al. | |
| 2017/0199971 A1 | 7/2017 | Yaddanapudi et al. | |
| 2020/0152322 A1 | 5/2020 | Yaddanapudi et al. | |

FOREIGN PATENT DOCUMENTS

| | | | |
|---|---|---|---|
| EP | 1308185 A2 | 5/2003 | |
| WO | 2007041014 A2 | 4/2007 | |
| WO | 2008013944 A2 | 1/2008 | |
| WO | 2015196109 A2 | 12/2015 | |

OTHER PUBLICATIONS

Office Action for U.S. Appl. No. 16/738,402 dated Apr. 30, 2020 Apr. 30, 2020.
Baker et al., "Use of an amorphous silicon electronic portal imaging device for multileaf collimator quality control and calibration", Physics in Medicine and Biology, 2005, pp. 1377-1392, vol. 50 2005.
Budgell, et al., "Daily Monitoring of Linear Accelerator Beam Parameters Using an Amorphous Silicon EPID", Physics in Medicine and Biology, Mar. 2007, pp. 1721-1733, vol. 52, No. 6 2007.
Chang et al., "Use of EPID for leaf position accuracy QA of dynamic multileaf collimator (DMLC) treatment", Medical Physics, 2004, pp. 2091-2096, vol. 31 2004.
Das et al., "Accelerator Beam Data Commissioning Equipment and Procedures: Report of the TG-106 of the Therapy Physics Committee of the AAPM", Medical Physics, Sep. 2008, pp. 4186-4215, vol. 35, Issue 9 2008.
Dirkx et al., "Daily dosimetric quality control of the MM50 Racetrack Microtron using an electronic portal imaging device", Radiotherapy and Oncology, 1995, pp. 55-60, vol. 37 1995.
Extended European Search Report for EP Application 15810058.6 dated Feb. 2, 2018 2018.
Glide-Hurst et al., "Commissioning of the Varian TrueBeam linear accelerator: A multi-institutional study", Medical Physics, 2013, vol. 40 2013.
Goddu et al., "Verification of beam-line geometry of TrueBeam using MV-EPID", AAPM, 2013 2013.
Herman et al., "Clinical use of Electronic Portal Imaging: Report of AAPM Radiation Therapy Committee Task Group 58", Med. Phys., May 2001, pp. 712-737 2001.
International Preliminary Report on Patentabiity (Chapter I) for PCT/US2015/036749 dated Dec. 29, 2016 2016.
International Search Report and Written Opinion for PCT/US2015/036749 dated Jan. 8, 2016 2016.
Klaclova, T., Truebeam Machine Performance Check (MPC), Varian Oncology Systems, dated Apr. 19, 2013 2013.
Office Action for CN Application 201580044616.1 dated Dec. 20, 2018 2018.
Parent et al., "Evaluation of two methods of predicting MLC leaf positions using EPID measurements", Medical Physics, 2006, pp. 3174-3182, vol. 33 2006.
Prisciandaro et al., "Utilizing an electronic portal imaging device to monitor light and radiation field congruence", Journal of Applied Clinical Medical Physics, 2003, pp. 315-320, vol. 4 2003.
Samant et al., "Verification of multileaf collimator leaf positions using an electronic imaging device", Medical Physics, 2002, pp. 2900-2912, vol. 29 2002.
Sun et al., "A novel and comprehensive daily QA tool using MV-EPID and kV imagers", AAPM, 2013 2013.
Van Elmpt et al., "A Literature Review of Electronic Portal Imaging for Radiotherapy Dosimetry", Radiotherapy and Oncology, Sep. 2008, pp. 289-309, vol. 88, Issue 3 2008.
Vieira et al., "Fast and accurate leaf verification for dynamic multileaf collimation using an electronic portal imaging device", Medical Physics, 2002, pp. 2034-2040, vol. 29 2002.
Yang et al., "Quantitative measurement of MLC leaf displacements using an electronic portal imaging device", Physics in Medicine and Biology, 2004, pp. 1521-1533, vol. 49 2004.
Zheng et al., "Commissioning and Dosimetric Characteristics of TrueBeam System: Composite Date of Three TrueBeam Machines", Medical Physics, Nov. 2012, pp. 6981-7018, vol. 39, retrieved from <URL: http:/www.ncbi.nlm.nih.gov/pubmed/23127092> on Jun. 9, 2015 2015.

* cited by examiner

ACCEPTANCE, COMMISSIONING, AND ONGOING BENCHMARKING OF A LINEAR ACCELERATOR (LINAC) USING AN ELECTRONIC PORTAL IMAGING DEVICE (EPID)

CROSS-REFERENCE TO RELATED APPLICATIONS

This application is a divisional application of U.S. patent application Ser. No. 17/808,399, filed Jun. 23, 2022, which is a continuation application of U.S. patent application Ser. No. 17/212,065, filed Mar. 25, 2021, now U.S. Pat. No. 11,393,582 issued Jul. 19, 2022, which is a continuation application of U.S. patent application Ser. No. 16/738,402, filed Jan. 9, 2020, now U.S. Pat. No. 10,964,429, issued Mar. 30, 2021, which is a divisional application of U.S. patent application Ser. No. 15/320,599, filed Dec. 20, 2016, now U.S. Pat. No. 10,553,313, issued Feb. 4, 2020, which is a national phase application of International Patent Application Ser. No. PCT/US2015/036749, filed on Jun. 19, 2015, which claims the benefit of U.S. Provisional Patent Application Ser. No. 62/015,184, filed on Jun. 20, 2014, which are all incorporated herein by reference in their entireties.

BACKGROUND OF THE INVENTION

Many conventional methods for commissioning a linear accelerator (LINAC) equipped with an electronic portal image device (EPID) largely depend on individual testing environment and parameters. Because individual testing parameters are usually configured by an end user, certain levels of machine performance variability can be found, some leading to potentially questionable quality of patient treatments.

Likewise, for treatment planning systems (TPS) work, local institutions generally collect data and create their own plans and procedures for evaluation of a local TPS system. Because local data is unique to each local testing environment, any performance variability in the system is difficult to assess and evaluate due to the variability of input data and testing processes. Furthermore, in the perspective of an end user of TPS systems, it is not clear whether the performance variability in the system is caused by the variability of input data or an incorrect performance or configuration of TPS systems.

The present invention is directed to overcoming one or more of the problems set forth above.

SUMMARY OF INVENTION

This section provides a general summary of the disclosure and is not a comprehensive disclosure of its full scope or all of its features.

An aspect of this invention provides a system for acceptance testing and commissioning a LINAC (linear accelerator), said system comprising: a memory storing first reference data wherein said first reference data is collected from a reference machine composed of a LINAC and electronic portal imaging device (EPID), wherein said reference data represents at least changes in radiation measurement at said EPID of said reference machine in relation to changes in parameters of said LINAC of said reference machine; a testing machine composed of a LINAC and EPID; and a processor associated with said memory, wherein said processor is configured to execute an analysis software program wherein said analysis software program collects machine performance data from said testing machine wherein said machine performance data represents at least changes in radiation measurement at said EPID of said testing machine in relation to changes in parameters of said LINAC of said testing machine and compares said first reference data with said machine performance data to assess accuracy of said testing machine.

Another aspect of this invention provides a method for acceptance testing and commissioning a LINAC (linear accelerator), said method comprising: collecting first reference data from a reference machine composed of a LINAC and electronic portal imaging device (EPID) wherein said reference data represents at least changes in radiation measurement at said EPID of said reference machine in relation to changes in parameters of said LINAC of said reference machine; storing said first reference data in a memory associated with at least one processor; collecting machine performance data from a testing machine composed of a LINAC and EPID wherein said machine performance data represents at least changes in radiation measurement at said EPID of said testing machine in relation to changes in parameters of said LINAC of said testing machine; and comparing, with an analysis software program, said first reference data with said machine performance data to assess accuracy of said testing machine wherein said processor is configured to execute said analysis software program.

Still another aspect of this invention provides a system for acceptance testing and commissioning a treatment planning system (TPS), said system comprising: a memory storing standard reference data wherein said standard reference data is composed of a plurality of treatment plans and predetermined results of such treatment plans; and a processor associated with said memory having a test performance engine performing a plurality of standard tests based on standard input data and generating at least one test performance result for each standard test and an analysis software program comparing said test performance result with said standard reference data wherein said test performance result is compared with at least one predetermined result of said treatment plan and determining whether each said test performance result meets a tolerance standard wherein said tolerance standard is a pre-determined standard corresponding to at least one of said standard tests, wherein said processor is configured to execute said test performance engine and analysis software program.

Yet another aspect of this invention provides a method for acceptance testing and commissioning a treatment planning system (TPS), said method comprising: collecting standard reference data wherein said standard reference data is composed of a plurality of treatment plans and predetermined results of such treatment plans; storing said standard reference data in a memory associated with at least one processor; performing, with a test performance engine, a plurality of standard tests based on standard input data wherein said test performance engine generates at least one test performance result for each standard test wherein said processor is configured to execute said test performance engine; comparing, with an analysis software program, said test performance result with said standard reference data wherein said test performance result is compared with at least one predetermined result of said treatment plan wherein said processor is configured to execute said analysis software program; and determining, with said analysis software program, whether each said test performance result meets a tolerance standard wherein said tolerance standard is a pre-determined standard corresponding to at least one of said standard tests.

Another aspect of this invention provides the method for acceptance testing and commissioning the treatment planning system (TPS) as described the paragraph immediately above, wherein said steps of performing, comparing, and determining are performed by a software application wherein said software application comprises said test performance engine and said analysis software program.

Another aspect of this invention provides the method for acceptance testing and commissioning the treatment planning system (TPS) as described in the paragraph immediately above, wherein said software application is configured to automatically perform said steps of performing, comparing, and determining.

Another aspect of this invention provides the method for acceptance testing and commissioning the treatment planning system (TPS) as described in the paragraph immediately above, wherein said software application is configured to perform said steps of performing, comparing, and determining in a pre-determined time interval.

Another aspect of this invention provides the method for acceptance testing and commissioning the treatment planning system (TPS) as described in the paragraph that is located three paragraphs above this paragraph, wherein said analysis software program is configured to automatically communicate to a medical service provider of said test performance result when said test performance result fails to meet said tolerance standard.

Another aspect of this invention provides the method for acceptance testing and commissioning the treatment planning system (TPS) as described in the paragraph that is located four paragraphs above this paragraph, wherein said software application resides on a service-based system wherein said standard reference data is stored in said service-based system.

Another aspect of this invention provides the method for acceptance testing and commissioning the treatment planning system (TPS) as described in the paragraph that is located six paragraphs above this paragraph, wherein said standard input data comprises standard beam data, standard images data, standard contour data, and standard treatment plans.

In yet another aspect, this invention provides the system for acceptance testing and commissioning the treatment planning system (TPS) as described in the paragraph that is located eight paragraphs above this paragraph, wherein said test performance engine and analysis software program are configured to automatically perform said processes of performing said standard tests, comparing said test performance result with said standard reference data, and determining whether said test performance results meets a tolerance standard.

Another aspect of this invention provides the system for acceptance testing and commissioning the treatment planning system (TPS) as described in the paragraph immediately above, wherein said test performance engine and analysis software program are configured to automatically perform said processes of performing said standard tests, comparing said test performance result with said standard reference data, and determining whether said test performance results meets a tolerance standard in a pre-determined time interval.

Another aspect of this invention provides the system for acceptance testing and commissioning the treatment planning system (TPS) as described in the paragraph that is located two paragraphs above, wherein said test performance engine and analysis software program are configured to automatically communicate to a medical service provider of said test performance result when said test performance result fails to meet said tolerance standard.

Another aspect of this invention provides the system for acceptance testing and commissioning the treatment planning system (TPS) as described in the paragraph that is located eleven paragraphs above this paragraph, wherein said test performance engine and analysis software program reside on a service-based system wherein said reference data is stored in said service-based system.

Another aspect of this invention provides the system for acceptance testing and commissioning the treatment planning system (TPS) as described in the paragraph that is located twelve paragraphs above this paragraph, wherein said standard input data comprises standard beam data, standard images data, standard contour data, and standard treatment plans.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings. The description and specific examples in this summary are intended for purposes of illustration only and are not intended to limit the scope of the present disclosure.

BRIEF DESCRIPTION OF DRAWINGS

The drawings described herein are for illustrative purposes only of selected embodiments and not all possible implementations, and are not intended to limit the scope of the present disclosure.

Figure 1:
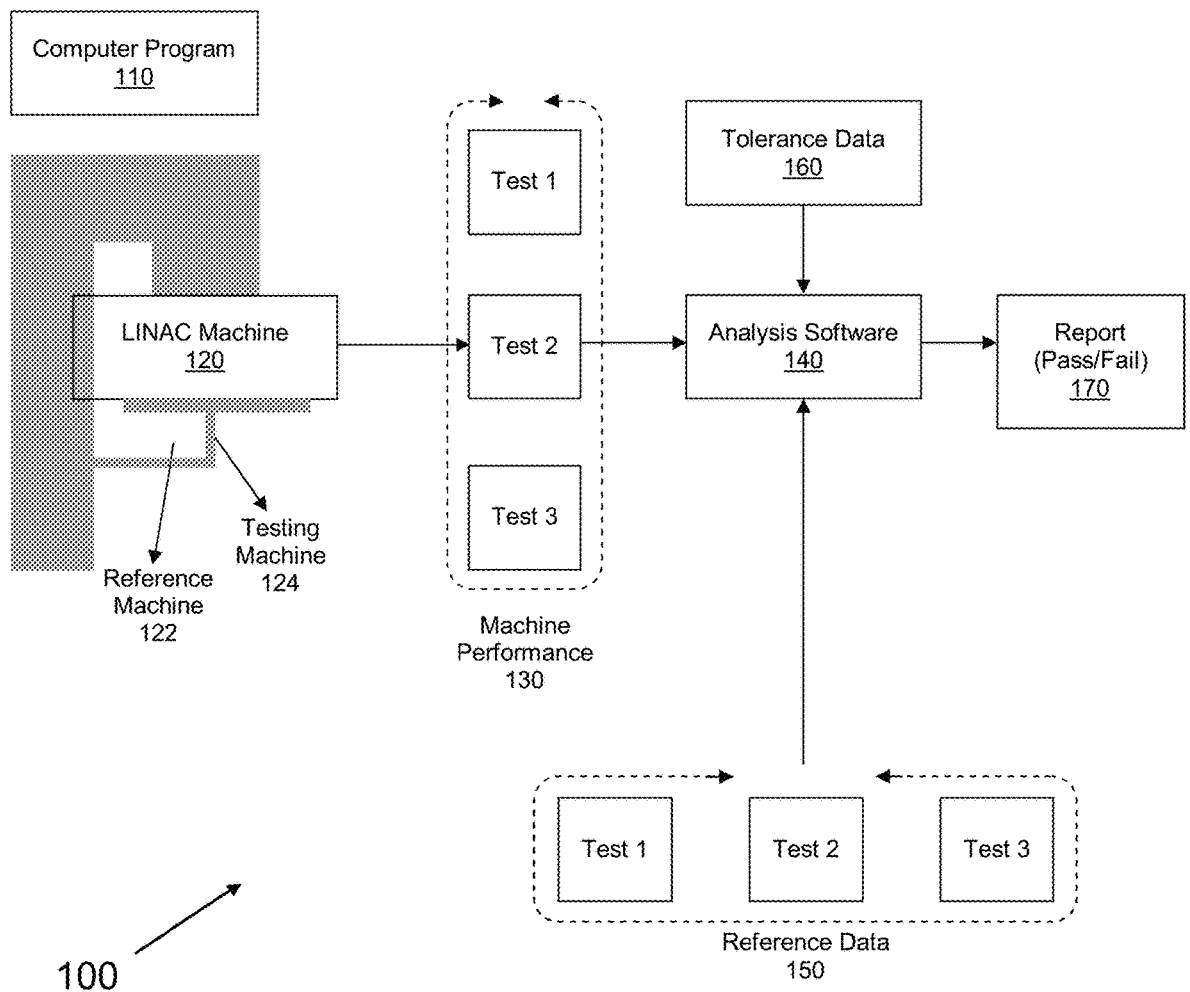
FIG. 1 illustrates a schematic block diagram of a system for acceptance testing and commissioning of a LINAC according to an illustrative, but nonlimiting, exemplary embodiment.

Reference characters in the written specification indicate corresponding items shown throughout the drawing figures.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

1. EPID-Commissioning

FIG. 1 is a schematic block diagram of an illustrative, but nonlimiting, system 100 for an exemplary embodiment of an EPID-commissioning system. The illustrative, but nonlimiting, exemplary system of FIG. 1 may include a computer program 110, a LINAC machine 120, machine performance data 130, analysis software 140, reference data 150, tolerance data 160, and a pass/fail report 170.

The computer program 110 can comprise any computer program code adapted to control the processes of acceptance testing and commissioning of the LINAC machine 120 as described herein. In the exemplary embodiment, the computer program 110 is comprised of an extensible markup language (XML) code. It should be understood, however, that any other suitable program languages such as C/C++, Java, etc., can be used to encode the computer program 110.

The LINAC machine 120 includes at least a LINAC and an electronic portal imaging device (EPID). The LINAC of the LINAC machine 120 is a typical LINAC that generates various types of radiation beams (e.g., MV photon beams, kV photon beams, flattened and unflattened beams, electron beams, gamma ray beams (for non-LINAC applications of the present invention, etc.) used for various medical purposes. For example, certain types of radiation beams are used for therapy purposes while other types of radiation beams are used for imaging purposes. The LINAC can be controlled with a number of different parameters such as internal machine configuration changes and beam modifier insertion. The machine configuration changes include beam energy, radiation type, field size, multi leaf collimator shape, beam fluence alteration, medical purpose, etc. The beam modifiers include wedges, compensating filters, phantoms, etc., that can be inserted into the beam of a LINAC. The effect of these changes on characteristics of a LINAC beam can be evaluated with in-air and\or with in-phantom measurements.

In the exemplary embodiment, the LINAC machine 120 can be a reference machine 122 or a testing machine 124. The reference machine 122 is used to collect the reference data 150 for acceptance testing and commissioning. Preferably, the reference machine 122 is fully calibrated and adjusted based on an industry standard. For example, the LINAC and EPID of the reference machine 122 can be calibrated and validated according to one of the standards provided by the Accredited Dosimetry Calibration Laboratory (ADCL). However, it should be understood that any suitable method or standard for calibration can be used for purposes stated herein. The testing machine 124 is a LINAC machine that is being tested and commissioned by the proposed method or system.

The reference data 150 preferably represents a correlation between the parameters and radiation measurement of the reference machine 122 (i.e., representative of a properly configured LINAC machine). For example, the reference machine 122 detects differences in radiation measurement at the EPID of the reference machine 122 in relation to any changes (changing individual parameters on a LINAC by known amounts) made to the parameters of the LINAC of the reference machine 122. In this way, the system 100 is configured to keep track of relative differences in radiation measurement at the EPID caused by changing the parameters of the LINAC. In the exemplary embodiment, the radiation measurement can include point radiation doses, dose profiles, planar dose distributions, percent depth doses, and three-dimensional dose distributions. It should be understood that the radiation measurement can include other types of information/data relating to the performance of a LINAC. In the exemplary embodiment, the reference data 150 can be stored in a memory residing on the system 100. Alternatively, any external memory device can be used to store the reference data 150.

The proposed EPID based data collection relies on acquiring two dimensional electronic images of radiation beams. These images can be collected with and without test phantoms in the path of an evaluated beam. Images of various beam modifiers (e.g., wedges, compensating filters, etc.) can be collected as well. By being able to relate the EPID images to a nominal performance of a LINAC through reference data, the images collected with EPID can be used to evaluate an individual machine against an expected performance. By knowing how the reference data is affected by changing of various LINAC parameters, EPIDs can also be used to characterize a LINAC machine which has not previously been evaluated.

In the exemplary embodiment, the system 100 can comprise multiple reference machines 122 to collect multiple sets of reference data 150 to increase accuracy and reliability of commissioning. For example, the system 100 can be configured to average the values of multiple sets of reference data 150 obtained from multiple reference machines 122 and use that average value as the reference data 150 for purposes of commissioning a testing machine 124 as stated herein.

The machine performance data 130 preferably represents a correlation between the parameters and radiation measurement of the testing machine 124. Like the reference machine, the testing machine 124 measures differences in radiation measurement at the EPID of the testing machine 124 in relation to any changes made to the parameters of the LINAC of the testing machine 124. In the exemplary embodiment, the machine performance data 130 can be stored in a memory residing on the system 100. Alternatively, any external memory device can be used to store the machine performance data 130.

The machine performance data 130 is compared with the reference data 150 in order to assess whether the LINAC of the testing machine 124 accurately generates a proper amount of radiation according to input data provided by the user. In the exemplary embodiment, the analysis software 140 performs such comparison. The analysis software 140 is configured to compare the collected machine performance data 130 with the reference data 150 and determine whether the machine performance data 130 matches the reference data 150 within certain acceptance criteria. If the difference between the machine performance data 130 and the reference data 150 falls into that acceptable range of criteria, then the system 100 determines that the testing machine 124 is operating accurately.

This inventive concept relies on relative tests, comparison with the reference data 150, and a set of established tolerances to characterize performance of a LINAC. In this process, the collected machine performance data 130 does not have to be fully corrected and can contain asymmetries and other artifacts associated with backscatter and position of an EPID during the collection of data. The reference data 150 which was generated from the reference machine 122 with EPID in the same position contains the same artifacts, and thus, as long as the images/radiation measurement at the EPID of the testing machine 124 matches within the established tolerances, the testing machine 124 would be deemed acceptable for clinical use.

The established tolerances are not based on conventional dosimetric tolerances in radiotherapy (i.e., 3%/3 mm or 2%/2 mm, etc.) but rather are a set of conversion factors. These factors, when applied to the machine performance data 130, can produce conventional dosimetric tolerances which are applied to data collected or calculated using the conventional dosimetric equipment to assess the physical machine energy and dose profiles. The relationship between the machine performance data 130 and the reference data 150 can be defined by:

[(Machine Performance Data (130))/(Reference Data (150))]*(Tolerance Data (1) (160)=Conventional Acceptance Criteria It should be understood that Equation (1) is provided only as an example and should not be used to limit the scope of the present invention. Any other method or mathematical equation suitable to quantify the relationship between the machine performance data 130 and the reference data 150 in a manner that is consistent with the descriptions provided herein can be also used.

In this exemplary embodiment, the tolerance data 160 represents a predetermined relationship between radiation measured by the EPID of the reference machine 122 and radiation measured by a conventional standard method (i.e., standard water tank measurement). For example, a conventional standard method can be one of the methods/reports issued by the American Association of Physicists in Medicine (AAPM) Task Groups. In the exemplary embodiment, the tolerance data 160 can be stored in a memory residing on the system 100. Alternatively, any external memory device can be used to store the tolerance data 160. The conventional standard method is used to collect data for LINAC commissioning by scanning 1 D, 2D, and/or 3D images from a water tank. Any conventional data collection method which can be utilized by one of ordinary skill in the art can be also used for purposes of collecting data.

After comparing the machine performance data 130 with reference data 150, the analysis software 140 generates a pass/fail report 170. If the machine performance data 130 matches the reference data 150 within acceptable criteria then the analysis software 140 generates a pass report. If the machine performance data 130 does not match the reference data 150 within acceptable criteria then the analysis software 140 generates a fail report.

In the exemplary embodiment, the computer program 110 can be configured to automate the process of acceptance testing and commissioning. For example, the computer program 110 can be configured to automatically drive the testing machine 124 to collect the machine performance data 130 and drive the analysis software 140 to compare the reference data 150 with the machine performance data 130 to assess the accuracy of the testing machine 124. Furthermore, the computer program 110 can be configured to automatically generate the pass/fail report 170.

In one embodiment, the computer program 110 can be implemented in a local computer application that can reside on the LINAC machine 120. In this embodiment, other components of the system 100 such as the analysis software 140, machine performance data 130, tolerance data 160, and/or the reference data 150 can also reside on the LINAC machine 120. The LINAC machine can be configured to include a memory that can store the reference data 150, the machine performance data 130, and/or the tolerance data 160.

In an alternative embodiment, the computer program 110 can reside on an external device or computer (not shown). The external device can be configured to communicate with the LINAC machine 120 and/or the analysis software 140. In this embodiment, a user can control the LINAC machine 120 via the external device which preferably includes appropriate input, output, and/or display devices. Alternatively, the analysis software 140 or other data such as the machine performance data 130, the reference data 150, and/or the tolerance data 160 can also reside on the external device or computer.

In another alternative embodiment, the analysis software 140 can be implemented in a service-based system. The service-based system preferably provides network accessibility to the users of the system 100. In this embodiment, the users of the system 100 are capable of accessing and analyzing the reference data 150, tolerance data 160, machine performance data 130, and/or pass/fail report 170 stored in the service-based system. For example, the system 100 provides an environment for benchmarking a set of reference data available for other similar machines. Any user with proper authority can access the service-based system where the reference data 150 is stored and can benchmark the reference data 150 for calibration of their LINAC machines. The service-based system can be configured as a cloud network but any other computing network with suitable networking capability can be implemented.

Figure 2:
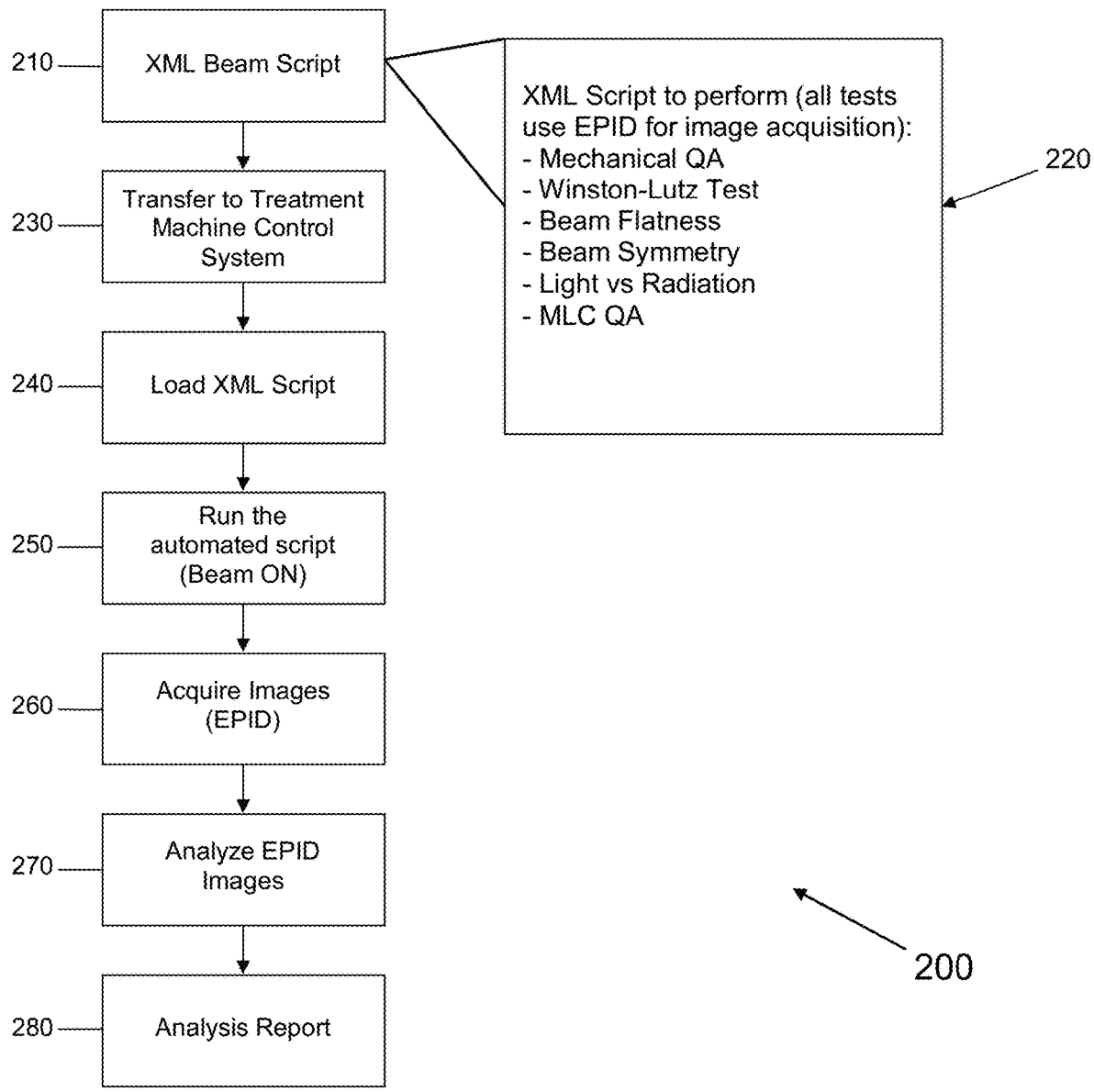
FIG. 2 illustrates a workflow of the computer program 110 of FIG. 1 for an illustrative, but nonlimiting embodiment.

FIG. 2 illustrates an exemplary workflow of the computer program 110 of FIG. 1 and is generally indicated by numeral 200. In the description of the flowcharts, the functional explanation marked with numerals in angle brackets, <nnn>, will refer to the flowchart blocks bearing that number. In this illustrative, but non-limiting exemplary workflow, the computer program 110 is comprised of an XML code. An XML beam script is encoded first <210>. The XML beam script is coded to perform a variety of tests that can be performed by an EPID, for example, mechanical QA (quality assurance), Winston-Lutz test, Beam Flatness test, Beam Symmetry test, Light-Radiation comparison test, and MLC QA <220>. It should be understood that these tests are introduced only as an example and should not be used to limit the scope of the present invention. Any other test suitable for testing an EPID can be encoded as part of the beam script.

Next, the XML script is transferred and loaded to the treatment machine control system 100 (or the LINAC machine 120) <230>. In the alternative embodiment, the XML script can be loaded <240> to the external device (not shown). The system 100 (or the LINAC machine 120) is configured to run or execute the automated XML script <250> in a mode that may be designated as "BeamON" mode, and subsequently operates the testing machine 124 to acquire images from the EPID <260>.

Next, the XML script loaded to the system 100 <240> (or the LINAC machine 120) is operated to control the analysis software 140 in order to analyze the EPID-captured images <270> of radiation. The XML script loaded to the system 100 (or the LINAC machine 120) finally is executed to produce the pass/fail report 170 based on the analysis performed by the analysis software 140 <280>.

In an alternative embodiment, the XML script can be loaded to the external device or computer as described above. In this alternative embodiment, the external device can be configured to communicate with the LINAC machine 120 to execute the processes described above in conjunction with FIG. 2.

In another alternative embodiment, the XML script can be loaded to the service-based system as described above. In this alternative embodiment, the XML script can be configured to automatically control the steps described in conjunction with FIG. 2 at the service-based system. The users of the system 100 can access the service-based system and commission their testing machine by using the automated XML script that resides on the service-based system.

Figure 3:
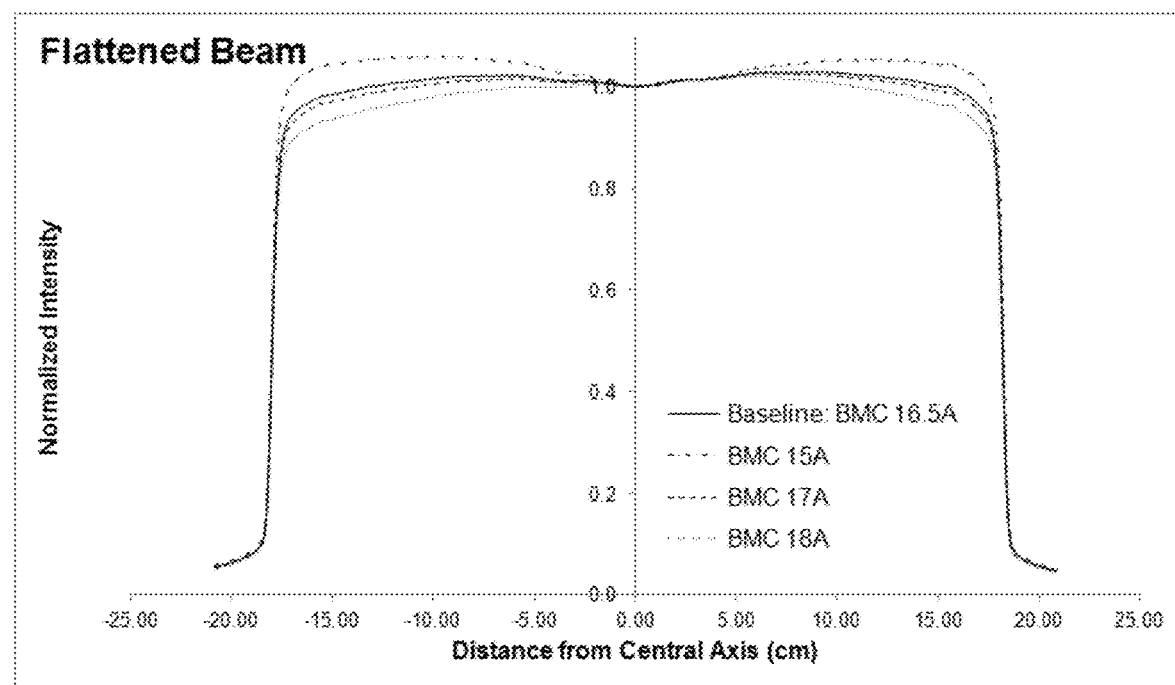
FIG. 3 illustrates an example of relative measurements performed by the LINAC machine 120 of FIG. 1 utilizing a photon radiation beam for an illustrative, but nonlimiting embodiment.

FIG. 3 illustrates an example of relative measurements performed by the LINAC machine 120 of FIG. 1 using a photon radiation beam. The data in FIG. 3 was collected for open field photon beams. In FIG. 3, beam energy changes, e.g., percent depth dose, over the full range of adjustment were measured by the LINAC machine 120. FIG. 3 shows how beam energy changes were detected with relative measurements. A set of tolerance data relates the relative measurements and changes to absolute tolerances. Open field images were obtained at the EPID of the LINAC machine 120 at different bending magnet current settings. Based on the measurements, FIG. 3 shows the flatness of the beam changes when compared against the baseline data. The flatness of photon beams is extremely sensitive to change in energy of the incident beam. A small change in the penetrative quality of a photon beam results in very large change in beam flatness. The proposed system of FIG. 1 uses similar relative measurements to characterize the reference machine 122 in the new paradigm for acceptance and commissioning of a LINAC 120 machine where these relative changes can be related to absolute energy changes and conventionally established tolerances.

Figure 3A:
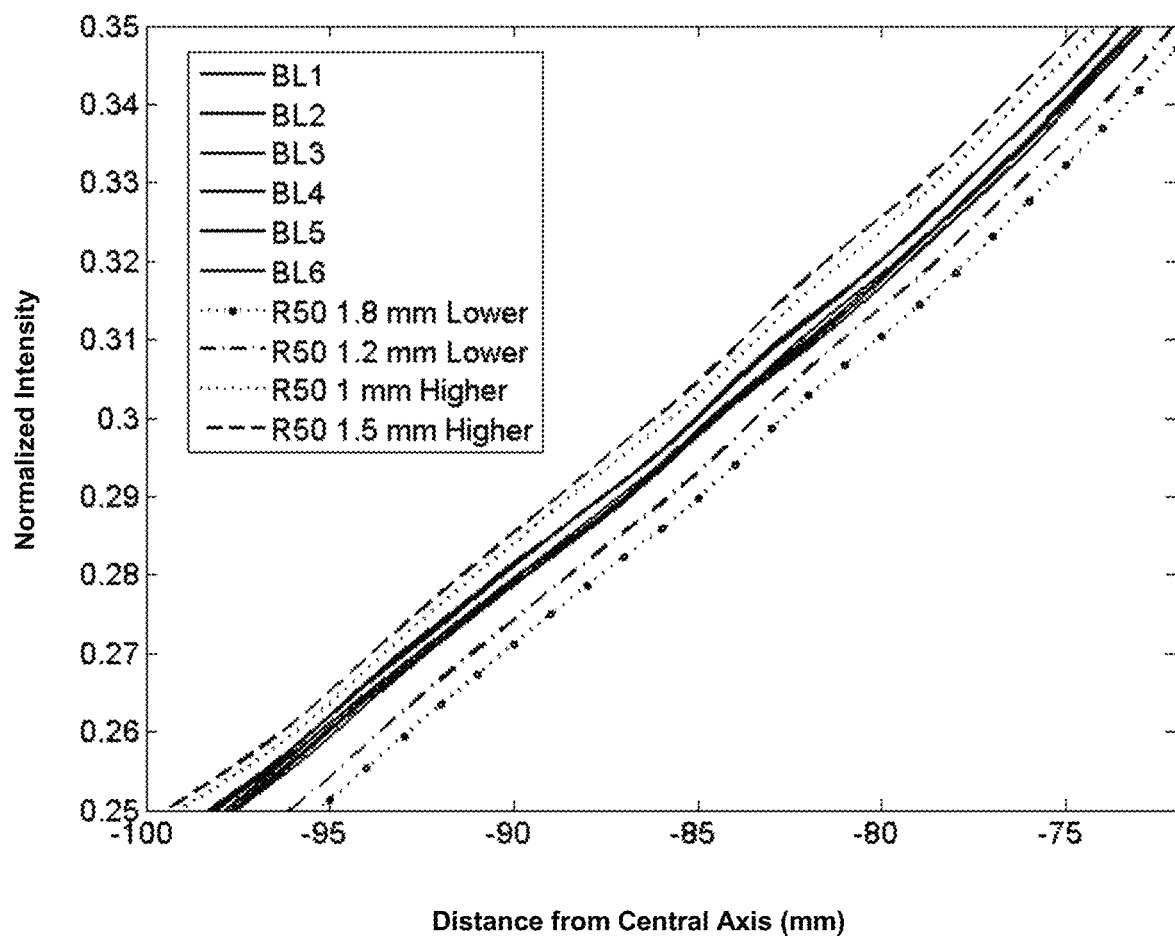
FIG. 3A illustrates an alternative example of relative measurements performed by the LINAC machine 120 of FIG. 1 utilizing an electron beam for an illustrative, but nonlimiting embodiment.

FIG. 3A illustrates an example of relative measurements performed by the LINAC machine 120 of FIG. 1 using an electron beam. The data in FIG. 3A shows a series of baseline measurements for an electron beam of the reference machine 122 showing the consistency in LINAC performance and repeatability of said measurements. The data shown in FIG. 3A also shows tolerance data measurements for energies which are high and low with respect to the nominal baseline energies. The data in FIG. 3A was collected with a small plastic wedge inserted in the electron beam. The plastic wedge in these measurements is only for illustrative purposes. It should be understood that objects other than the plastic wedge can be inserted into the beam to enhance the sensitivity and ease of the said measurements. It should also be understood that these objects can be made of materials other than plastic and that any object which creates differential radiation fluence or increases radiation sensitivity can be used. The data shown in FIG. 3A demonstrates ability of the proposed system of FIG. 1 to be used for acceptance testing and commissioning of electron beams of a LINAC machine 120 relative to the reference machine 122.

Figure 4:
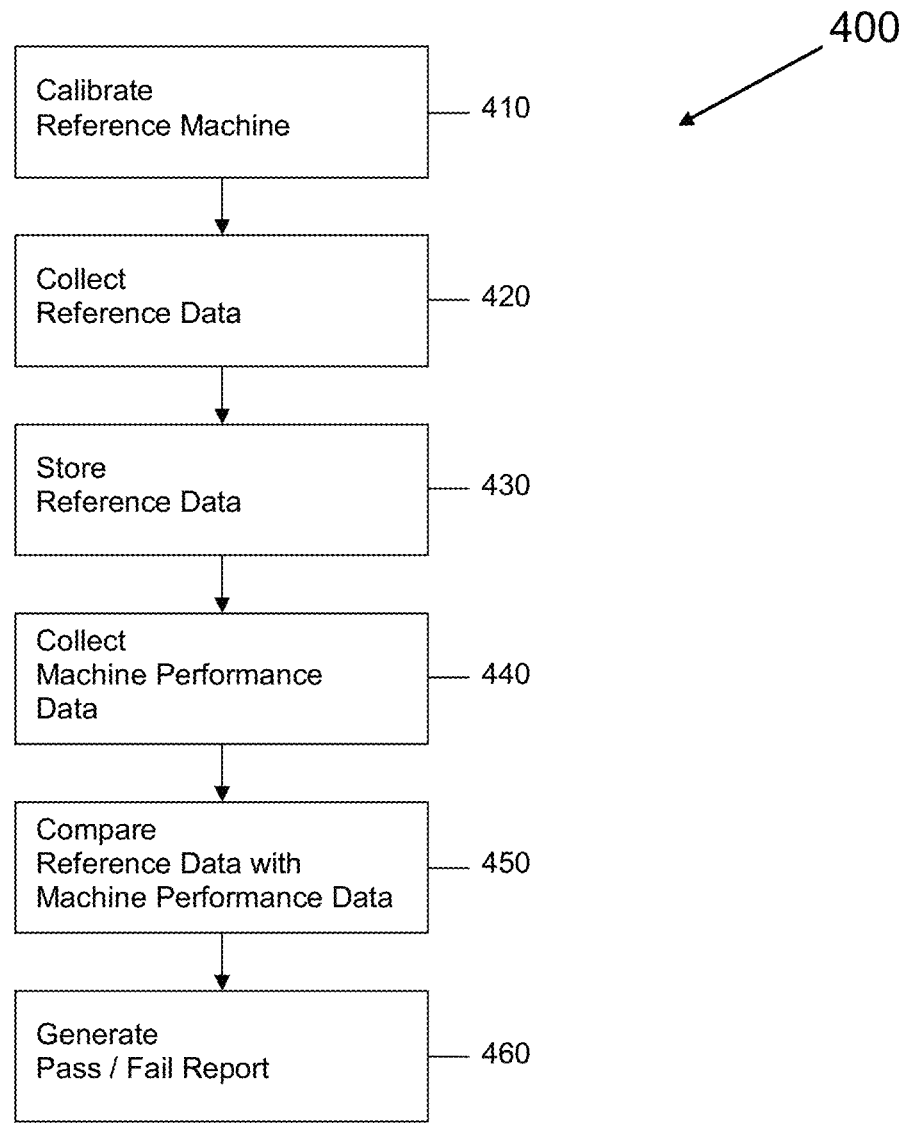
FIG. 4 illustrates a flowchart of a method for acceptance testing and commissioning of a LINAC according to an illustrative, but nonlimiting, exemplary embodiment.

FIG. 4 illustrates a flowchart of a method for acceptance testing and commissioning of a LINAC according to an illustrative, but nonlimiting, exemplary embodiment and is generally indicated by numeral 400. At step <410>, a reference machine 122 is calibrated according to one of the industry standards, for example, the standards provided by the ADCL. At step <420>, the system 100 collects the reference data 150 from the reference machine 122. As described above, the reference data 150 represents a correlation between the parameters and radiation measurement of the reference machine 122. At step <430>, the system 100 stores the collected reference data 150 in a memory. At step <440>, the system 100 collects the machine performance data 130 from a testing machine 124. As described above, the machine performance data 130 represents a correlation between the parameters and radiation measurement of the testing machine 124. At step <450>, the system 100 analyzes accuracy of the testing machine 124 by comparing the reference data 150 with the machine performance data 130.

For example, the analysis software 140 of FIG. 1 compares the reference data 150 with the machine performance data 130 to determine the differences between two. If the differences are within acceptable criteria then the analysis software 140, at step <460>, generates a pass report 170. If the differences are not within acceptable criteria then the analysis software 140, at step <460>, generates a fail report 170. The acceptable criteria can be calculated by Equation (1) described above or any other compatible method that takes into account the relative relationship between the machine performance data 130 and the reference data 150. In the exemplary embodiment of FIG. 4, at least the steps <440>, <450>, and <460> can be automated by using the computer program 110 of FIG. 1 as described in FIG. 2. As shown in FIG. 2, the computer program 110 can be encoded to automate the steps of <440>, <450>, and <460>.

2. TPS Commissioning

Historically, the radiotherapy treatment planning system (TPS) commissioning and implementation relied on data specifically collected for individual LINAC or standard input data provided for a model of an individual LINAC. The acceptance testing and commissioning of treatment planning system were performed by medical physicists by inputting their own images or standard images provided for specific tests and then manually creating treatment plans and software steps to test the treatment planning system. As such, to the extent that variable data is provided to a TPS, its outputs are variable. Since all of local data is unique, any performance variability in the system is to some extent expected due to the variability of input data. The end user is then faced with analyzing result data and sorting out any performance variations caused by either the variability of input data or an incorrect performance or configuration of TPS software.

In the proposed method or system for TPS commissioning, a set of standard input data is collected and analyzed to create a set of reference data. By inputting standard input data and standard plans into a TPS, it is expected to have a standard set of results. Any variability in the expected results will be most likely due to an incorrect performance or configuration of a TPS. This process would improve the efficiency of TPS commissioning. In addition, any real problems with the system can be more readily identifiable and reliance on the expertise and competence of the end user for identifying actual system performance issues from performance variability due to the variability of input data can be reduced.

Figure 5:
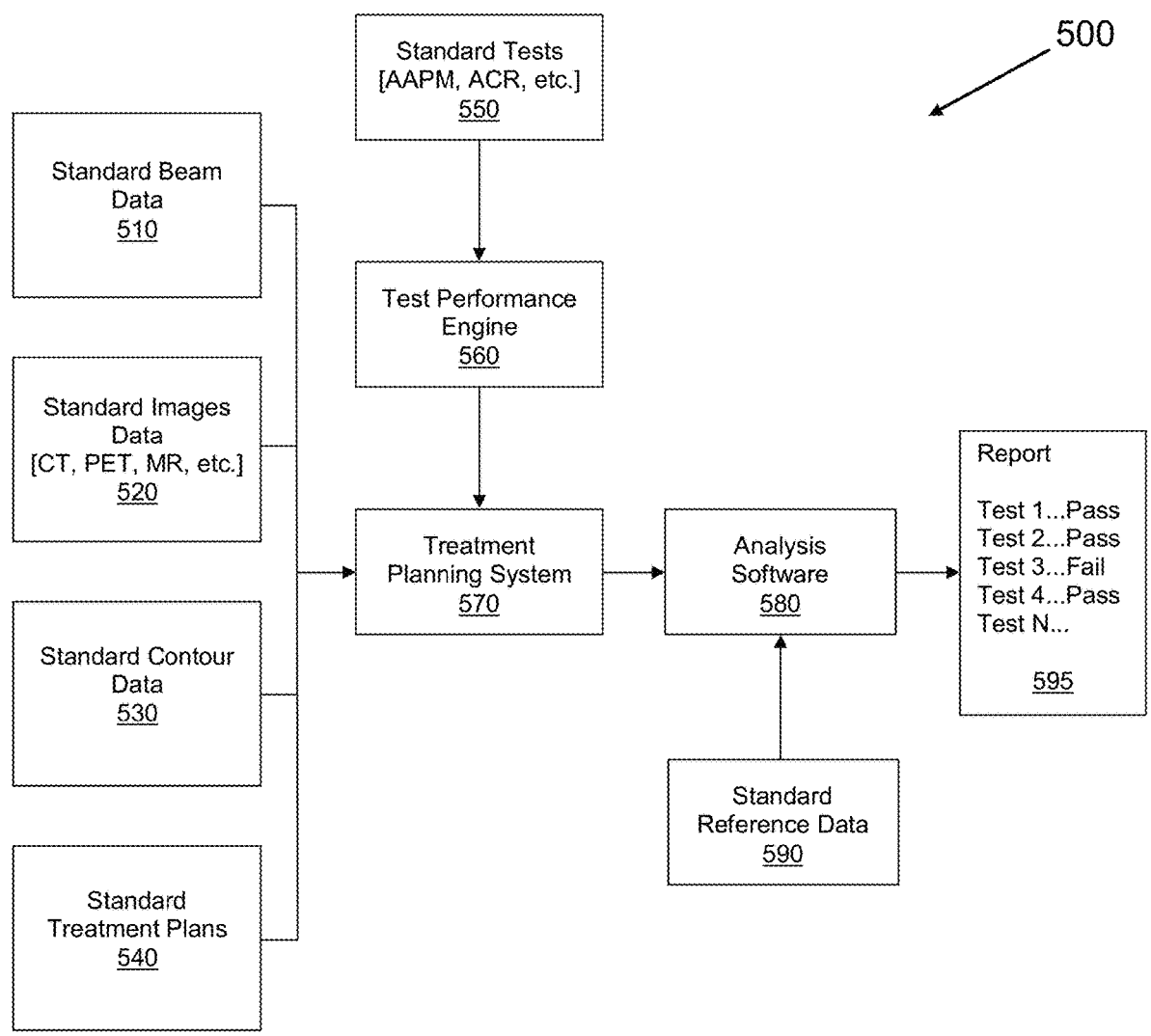
FIG. 5 illustrates a schematic block diagram of a system for acceptance testing and commissioning of a TPS system according to an illustrative, but nonlimiting, exemplary embodiment.

FIG. 5 is a schematic block diagram of an illustrative, but nonlimiting, system for an exemplary embodiment of a TPS commissioning system that is generally indicated by numeral 500. The illustrative, but nonlimiting, exemplary system of FIG. 5 may include standard beam data 510, standard images data 520, standard contour data 530, standard treatment plans 540, standard tests 550, a test performance engine 560, a treatment planning system 570, analysis software 580, standard reference data 590, and a pass/fail report 595.

In the exemplary embodiment, the system 500 collects the standard reference data 590. The standard reference data 590 is comprised of a plurality of standard treatment plans and their corresponding predetermined results. The predetermined results of standard treatment plans are collected by inputting standard input data to the system 500 and performing various TPS functions with the standard input data. For example, the standard treatment plans are performed by the treatment planning system 570 that takes the standard input data as an input. The treatment planning system 570 is configured to collect the results of the standard treatment plans. The standard input data comprises the standard beam data 510, standard images data 520, standard contour data 530, and/or standard treatment plans 540. The standard beam data 510 can comprise any data representing various information about radiation, e.g., quality, beam energy, radiation type, profiles, etc., in relation to a LINAC. The standard image data 520 can comprise any data representing images of phantoms or humans captured with computed tomography imaging, magnetic resonance imaging, positron emission tomography, etc. The standard contour data 530 can comprise any data representing the typical contour of a human body to which radiation is applied and/or contours applied to unique features of individual phantoms. The standard treatment plans 540 can comprise any data representing standard plans of applying radiation to a human body for medical purposes and/or to phantoms for testing of specific performance parameters of TPS. It should be understood that any other suitable type of information/data can be used to represent standard input data for this exemplary embodiment. The examples of the standard input data provided herein should not be used to limit the scope of the present invention. The standard reference data 590 and the standard input data can be stored in a memory (not shown) residing on the system 500. Alternatively, any external memory device can be used to store the standard reference data 590 and the standard input data.

After the collection process is completed, the system 500 performs a commissioning process. In the exemplary embodiment, the test performance engine 560 is configured to perform standard tests 550 using the standard input data such as the standard beam data 510, standard images data 520, standard contour data 530, and/or standard treatment plans 540 as an input. The standard tests 550 comprise various tests recommended by professional medical societies, regulatory bodies, and other agencies such as the AAPM and ACR.

The results of the standard tests 550 are analyzed by the analysis software 580. The analysis software 580 compares actual test performance results of the standard tests 550 with predetermined results of the standard treatment plans as represented by the standard reference data 590 and determines whether each test performance result meets a certain tolerance standard. The tolerance standard defines pre-determined acceptance criteria for corresponding standard tests. Preferably, the tolerance standard can be one of the published standards, for example, provided by the AAPM Task Groups. If the test performance result meets the tolerance standard that corresponds to the performed standard test 550 then the analysis software 580 generates a pass report 595. If the test performance result fails to meet the tolerance standard that corresponds to the performed standard test then the analysis software 580 generates a fail report 595.

In the exemplary embodiment, the test performance engine 560 can be configured to automatically perform the testing of standard tests 550, comparing the test performance results with the reference data 150, and/or determining whether the test performance results meet the tolerance standard.

The system 500 may include a software application (not shown) that comprises the test performance engine 560 and/or analysis software 580. In this embodiment, the software application can be configured to automate the processes of performing the standard tests 550, comparing the test performance results with the reference data, and determining whether the test performance results meet the tolerance standard. Alternatively, the software application can be configured to automatically perform such steps in a predetermined time interval. In this embodiment, the user of the system 500 can be provided with a user interface which can be used to enter a proposed interval time into the system 500. The predefined time interval could be set to correspond with testing requirements and recommendations provided by regulatory bodies, national and international organizations, and various medical societies, for example. Furthermore, the software application can be configured where use of software or an explicit override is required when any of the automatic and predefined tests fail to meet the tolerance standard.

This embodiment of integrated and automatic testing would significantly improve the reliability of system implementation, testing integrity and reliability, conformance of testing requirements and testing frequency, and communication and transparency of system functionality and configuration. This exemplary embodiment can automatically prevent use of unsafe and/or substandard treatment planning systems. Furthermore, the automatic testing significantly lessens the reliance on the expertise of the end users for test performance and result analysis and interpretation. As such, the developed system would ensure correct and consistent operation of treatment planning systems independent of the end user experience, training, and proficiency levels.

In another embodiment, the system 500 or the analysis software 580 can be configured to automatically communicate with a medical service provider, e.g., hospital staff, administration, manufacturer, or other stakeholders, to inform a test performance result when the test performance result is determined to be failing to meet the tolerance standard. In this embodiment, any communication means can be employed to provide data connection between the system 500 and a medical service provider such as the Internet, wireless network, cellular network, fax, conventional telephone line, etc.

In another alternative embodiment, the system 100 of EPID commissioning can be interfaced with the system 500 of TPS commissioning. A set of automatic test routines for testing the LINAC machine 120 of FIG. 1 and the treatment planning system 570 can be configured to ensure consistency between two systems and any changes or modifications in either the LINAC machine 120 or the treatment planning system 570 can be directly coupled to testing of the other system to ensure consistency of operation. The results of LINAC test analysis by the analysis software 140 of FIG. 1 can be used to automatically drive testing of treatment planning system 570 of FIG. 5 and conversely, the results of treatment planning system tests obtained from the analysis software 580 of FIG. 5 can be used to drive testing of LINAC machine 120 of FIG. 1. This approach ensures codependence of system performance between the LINAC machine 120 and the treatment planning system 570 and therefore significantly increases the confidence and accuracy of patient treatments. For example, the testing machine 124 that has been commissioned by the system 100 of FIG. 1 can be used to perform one of the standard tests of FIG. 5 and any pass/fail report generated by the analysis software 140 of FIG. 1 can be used for the system 500 in determining whether certain standard tests are performed with a validated LINAC. Conversely, standard beam data 510 and/or standard reference data 590 from FIG. 5 can be used to generate tolerance data 160 in FIG. 1, therefore closing the loop between the configuration and performance of LINAC and TPS.

In another alternative embodiment, the testing performance engine 560 and/or analysis software 580 can be implemented in a service-based system. The service-based system preferably provides network accessibility to the users of the system 500. In this embodiment, the users of the system 500 are capable of accessing and analyzing the standard input data, standard tests 550, standard reference data 590, and/or pass/fail report 595 stored in the service-based system. For example, the system 100 provides an environment for benchmarking a set of standard reference data 590 available for other similar test planning systems. Any user with proper authority can access the service-based system where the standard reference data 590 is stored and can benchmark the standard reference data 590 for calibration of their test planning systems. The service-based system can be configured as a cloud network but any other computing network with suitable networking capability can be implemented.

In this alternative embodiment, the system 100 of FIG. 1 and the system 500 of FIG. 5 can be connected to an external interface (manufacturer, cloud infrastructure, etc.) where the data and testing content of these systems are automatically updated. This embodiment would promote automatic updating of testing standard and requirements. Any changes in testing procedures, testing standards, testing tolerances, could be automatically and simultaneously deployed to all user sites ensuring timely implementation of any changes. Furthermore, with this approach, any regulatory (e.g., Federal Drug Administration) software recalls and audits can be automatically deployed, executed, and tested with the most up to data, procedures, and software. This approach would greatly increase the compliance with regulatory requirements and enforcements and would significantly improve confidence that all systems (either active or inactive) that are deployed in the field are functioning correctly.

Figure 6:
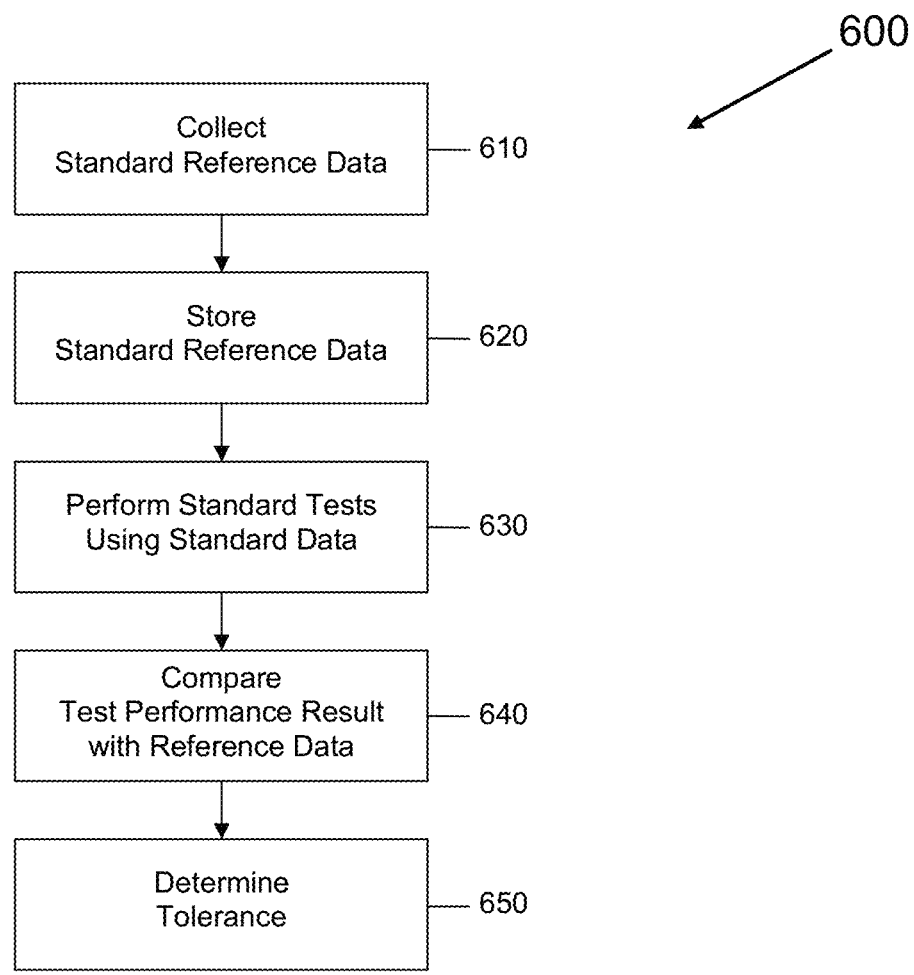
FIG. 6 illustrates a flowchart of a method for acceptance testing and commissioning of a TPS system according to an illustrative, but nonlimiting, exemplary embodiment.

FIG. 6 depicts a flowchart of a method for acceptance testing and commissioning of the TPS system 500 of FIG. 5 and is generally indicated by numeral 600. At step <610>, the system 500 collects the standard reference data 590. As described above, the standard reference data 590 comprises a plurality of standard treatment plans and their corresponding predetermined results. At step <620>, the system 500 stores the standard reference data in a memory. At step <630>, the test performance engine 560 of the system 500 performs the standard tests 550 using standard input data as an input. A test performance result corresponding to each standard test is generated. In this embodiment, at least one standard test can be configured to use the testing machine 124 of FIG. 1 in order to measure radiation generated by the LINAC of the testing machine 124. At step <640>, the analysis software 580 of the system 500 compares the test performance results of the standard tests 550 with the predetermined results of the standard treatment plans as represented by the standard reference data 590. At step <650>, the analysis software of the system 500 determines whether each test performance result meets a tolerance standard. In this exemplary embodiment, the test performance engine can be configured to automatically execute at least the steps of <630>, <640>, and <650>.

Furthermore, it should be understood that when introducing elements of the present invention in the claims or in the above description of the preferred embodiment of the invention, the terms "have," "having," "includes" and "including" and similar terms as used in the foregoing specification are used in the sense of "optional" or "may include" and not as "required." Similarly, the term "portion" should be construed as meaning some or all of the item or element that it qualifies.

Thus, there have been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. A method for acceptance testing and commissioning a treatment planning system (TPS), said method comprising:
    collecting standard reference data wherein said standard reference data is composed of a plurality of treatment plans and predetermined results of such treatment plans;
    storing said standard reference data in a memory associated with at least one processor;
    performing, with a test performance engine, a plurality of standard tests based on standard input data wherein said test performance engine generates at least one test performance result for each standard test wherein said processor is configured to execute said test performance engine;
    automatically comparing, with an analysis software program, said test performance result with said standard reference data wherein said test performance result is compared with at least one predetermined result of said treatment plan wherein said processor is configured to execute said analysis software program, wherein said comparing includes defining a relationship between said standard reference data and said test performance result; and
    automatically determining, with said analysis software program, and based on a result of said comparing, whether each said test performance result meets a tolerance standard wherein said tolerance standard is a pre-determined standard corresponding to at least one of said standard tests.

2. The method for acceptance testing and commissioning a treatment planning system (TPS) of claim 1, wherein said steps of performing, comparing, and determining are performed by a software application wherein said software application comprises said test performance engine and said analysis software program.

3. The method for acceptance testing and commissioning a treatment planning system (TPS) of claim 2, wherein said software application is configured to automatically perform said step of performing.

4. The method for acceptance testing and commissioning a treatment planning system (TPS) of claim 3, wherein said software application is configured to perform said steps of performing, comparing, and determining in a pre-determined time interval.

5. The method for acceptance testing and commissioning a treatment planning system (TPS) of claim 2, wherein said analysis software program is configured to automatically communicate to a medical service provider of said test performance result when said test performance result fails to meet said tolerance standard.

6. The method for acceptance testing and commissioning a treatment planning system (TPS) of claim 2, wherein said software application resides on a service-based system wherein said standard reference data is stored in said service-based system.

7. The method for acceptance testing and commissioning a treatment planning system (TPS) of claim 1, wherein said standard input data comprises standard beam data, standard images data, standard contour data, and standard treatment plans.

8. A system for acceptance testing and commissioning a treatment planning system (TPS), said system comprising:
 a memory storing standard reference data wherein said standard reference data is composed of a plurality of treatment plans and predetermined results of such treatment plans; and
 a processor associated with said memory having a test performance engine performing a plurality of standard tests based on standard input data and generating at least one test performance result for each standard test and an analysis software program automatically comparing said test performance result with said standard reference data wherein said test performance result is compared with at least one predetermined result of said treatment plan, wherein said comparing includes defining a relationship between said standard reference data and said test performance result and automatically determining based on a result of said comparing whether each said test performance result meets a tolerance standard wherein said tolerance standard is a pre-determined standard corresponding to at least one of said standard tests, wherein said processor is configured to execute said test performance engine and analysis software program.

9. The system for acceptance testing and commissioning a treatment planning system (TPS) of claim 8, wherein said test performance engine and analysis software program are configured to automatically perform said process of performing said standard tests.

10. The system for acceptance testing and commissioning a treatment planning system (TPS) of claim 9, wherein said test performance engine and analysis software program are configured to automatically perform said processes of performing said standard tests, comparing said test performance result with said standard reference data, and determining whether said test performance results meets a tolerance standard in a pre-determined time interval.

11. The system for acceptance testing and commissioning a treatment planning system (TPS) of claim 9, wherein said test performance engine and analysis software program are configured to automatically communicate to a medical service provider of said test performance result when said test performance result fails to meet said tolerance standard.

12. The system for acceptance testing and commissioning a treatment planning system (TPS) of claim 8, wherein said test performance engine and analysis software program reside on a service-based system wherein said reference data is stored in said service-based system.

13. The system for acceptance testing and commissioning a treatment planning system (TPS) of claim 8, wherein said standard input data comprises standard beam data, standard images data, standard contour data, and standard treatment plans.

* * * * *